United States Patent
Chopra et al.

(10) Patent No.: US 7,106,828 B2
(45) Date of Patent: Sep. 12, 2006

(54) X-RAY IMAGING USING PIXELATED GAS DETECTORS

(75) Inventors: Nasreen Gazala Chopra, Belmont, CA (US); Ronald L. Moon, Atherton, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 333 days.

(21) Appl. No.: 09/994,188

(22) Filed: Nov. 26, 2001

(65) Prior Publication Data

US 2003/0108151 A1    Jun. 12, 2003

(51) Int. Cl.
*H05G 1/64* (2006.01)

(52) U.S. Cl. .................. 378/98.8; 378/62; 250/374

(58) Field of Classification Search ............. 378/19, 378/62, 98.8; 250/385.1, 374, 381, 382, 250/378, 375, 380.1
See application file for complete search history.

(56) References Cited

U.S. PATENT DOCUMENTS

| | | | | |
|---|---|---|---|---|
| 3,418,474 A | * | 12/1968 | Spergel et al. | 250/385.1 |
| 4,096,389 A | * | 6/1978 | Ashe et al. | 378/7 |
| 4,276,476 A | * | 6/1981 | Cotic | 250/385.1 |
| 4,780,897 A | * | 10/1988 | McDaniel et al. | 378/62 |
| 5,119,408 A | * | 6/1992 | Little et al. | 378/4 |
| 5,308,988 A | * | 5/1994 | Siedband | 250/385.1 |
| 6,204,507 B1 | * | 3/2001 | Feige et al. | 250/372 |
| 6,362,484 B1 | * | 3/2002 | Beyne et al. | 250/374 |
| 6,476,397 B1 | * | 11/2002 | Francke | 250/385.1 |

OTHER PUBLICATIONS

Tiplier, Paul A. "Modern Physics," pp. 420-421.
Moy, Jean-Pierre, "Recent Developments inages 420-421 X-ray Imaging Detectors," pp. 27-37.
Li-Scholz, et al., "Atomic Data and Nuclear Data Tables—A Journal Devoted to Compilations of Experimental and Theoretical Results," pp. 181-212, 248, 266, 294, 298.

* cited by examiner

Primary Examiner—Edward J. Glick
Assistant Examiner—Irakli Kiknadze (57) ABSTRACT

X-ray imaging systems are provided. A representative x-ray imaging system includes a gas detector that is configured to retain a volume of gas. The gas detector incorporates a first detection circuit corresponding to a first region of the gas and a second detection circuit corresponding to a second region of the gas. The first detection circuit is adapted to provide a first signal indicative of an intensity of x-rays radiating into the first region of the gas and the second detection circuit is adapted to provide a second signal indicative of an intensity of x-rays radiating into the second region of the gas. Methods and other systems also are provided.

12 Claims, 9 Drawing Sheets

X-RAY IMAGING USING PIXELATED GAS DETECTORS

FIELD OF THE INVENTION

The present invention generally relates to x-ray imaging. More specifically, the invention relates to x-ray imaging systems and methods that involve the use of pixelated gas detectors.

DESCRIPTION OF THE RELATED ART

X-ray imaging has been used by the medical profession since the discovery of x-rays in the late nineteenth century. In particular, the medical profession typically uses still x-ray images of patients for diagnosing various ailments and conditions, such as broken bones. More recently, however, x-rays are being used in other manners, e.g., real-time imaging, and in various other applications. For instance, x-rays are being used by manufacturers to ensure quality of manufactured components and by security personnel to ensure that controlled items, such as firearms, are not able to enter designated areas.

X-ray imaging poses numerous technical challenges, particularly when being adapted for use in these recent applications. More specifically, known x-ray detection components that can be used in an x-ray imaging process suffer from various shortcomings. These shortcomings include limitations in the ability of x-ray detection components to be used in particular applications and difficulties associated with manufacturing the x-ray detection components.

For example, photographic films are limited in their application because they are not suitable for real-time imaging. Additionally, scintillators, which convert x-ray photons to light photons, are not ideal for use in low flux x-ray photon applications. In particular, when exposed to a low flux of x-ray photons, scintillators tend to exhibit resolution decay. Scintillators also typically suffer from manufacturing difficulties associated with producing large amorphous silicon panels. These panels are used to transfer images onto visible light detectors. Furthermore, photoconductors, which use x-ray photons to create electron-hole pairs, are difficult to manufacture. This is due, at least in part, to large crystal size requirements and/or low leakage current level requirements of the photoconductors.

Based on the foregoing, it can be appreciated that there is a need for x-ray imaging systems and methods that address these and/or other shortcomings of the prior art. For instance, there is a need for x-ray detection components that can be adapted for use in a variety of applications and/or can be manufactured without the complications currently encountered.

SUMMARY OF THE INVENTION

X-ray imaging systems and methods of the invention involve the use of pixelated gas detectors. Such pixelated gas detectors can be constructed using conventional semiconductor fabrication techniques. This potentially enables the gas detectors to be formed by readily available and relatively inexpensive batch-processing techniques.

Of particular interest, pixelated gas detectors of the invention may not be constrained by material limitations. For instance, the gas detectors may be formed with materials that can be selected based on the particular application. Thus, if a gas detector of a relatively large size is required, a material capable of being conveniently formed to the required size typically can be used.

A representative x-ray imaging system of the invention that incorporates a pixelated gas detector will now be briefly described. The gas detector of the x-ray imaging system is adapted to retain a volume of gas. The gas detector also incorporates a first detection circuit corresponding to a first region of the gas and a second detection circuit corresponding to a second region of the gas. The first detection circuit is adapted to provide a first signal indicative of an intensity of x-rays radiating into the first region of the gas. Likewise, the second detection circuit is adapted to provide a second signal indicative of an intensity of x-rays radiating into the second region of the gas.

By correlating the first signal(s) with a first pixel or group of pixels and, likewise, correlating the second signal(s) with a second pixel or group of pixels, embodiments of the gas detector can be used as digital gas detectors. That is, the gas detector can be used to provide information to a digital processor that converts the signals to image data. The image data then can be rendered to produce a digital x-ray image or series of real-time x-ray images.

In some embodiments, the various regions of gas retained by the gas detector are defined by separate chambers. These chambers can be interconnected so that the chambers pneumatically communicate with each other. In such a configuration, the gas retained by the chambers can be conveniently changed. More specifically, the gas detectors can include a gas inlet that pneumatically communicates with at least one of the chambers and selectively communicates with multiple reservoirs of gas. Preferably, each of the reservoirs contains a different type of gas. By selectively delivering gas from one of the reservoirs through the gas inlet and to the chambers, the gas of the chambers can be changed. This potentially changes the operating characteristics of the gas detector so that an improved signal corresponding to the detected x-rays can be produced.

Another representative imaging system includes a gas, which is susceptible to ionization, distributed to define plural imaging volumes arranged in an array. The imaging system also incorporates an ionization detector for providing indications of ionization of the gas for at least some of the imaging volumes. Additionally, an image generator is provided for converting the indications into an image.

A representative method for imaging with x-rays includes: providing a volume of gas; defining a first region of the gas and a second region of the gas, the first region of the gas being different than the second region of the gas; generating a first signal indicative of an intensity of x-rays radiating into the first region of the gas, the first signal corresponding to at least a first pixel; and generating a second signal indicative of an intensity of x-rays radiating into the second region of the gas, the second signal corresponding to at least a second pixel.

By generating additional signals indicative of the intensity of x-rays radiating into the first and second regions of the gas, sequential images can be generated. For instance, when this process is used to acquire images corresponding to an object, the sequential images can be real-time x-ray images that may be used for inspection of the object.

Another representative imaging method includes detecting ionization at respective gas volumes in an array of gas volumes and converting the ionization detected into an image.

Clearly, some embodiments of the invention may not exhibit one or more of the advantages and/or properties set forth above. Additionally, other systems, methods, features, and advantages of the invention will be or become apparent to one with skill in the art upon examination of the following drawings and detailed description. It is intended that all such additional systems, methods, features, and advantages be included within this description and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
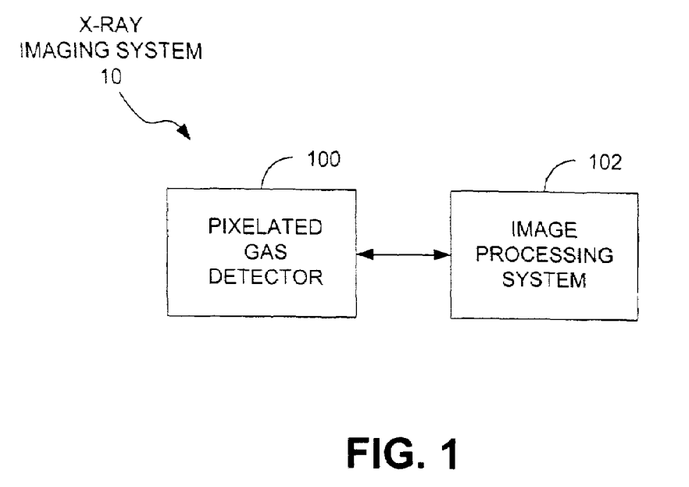
FIG. 1 is a schematic diagram of a representative embodiment of an x-ray imaging system of the invention.

Referring now to the figures, wherein like reference numerals indicate corresponding components throughout the several views, FIG. 1 schematically depicts a representative embodiment of an x-ray imaging system 10 of the invention. X-ray imaging system 10 includes a pixelated gas detector 100 and an image processing system 102. Note, the term "pixelated" is used herein to describe an association with one or more pixels, e.g., pixels of an image processing system.

As will described in greater detail, pixelated gas detector 100 is adapted to retain one or more volumes of gas, each of which can be associated with one or more pixels of the image processing system. More specifically, the pixelated gas detector uses each volume of gas to collect information regarding the intensity of x-rays radiating through that volume of gas. Since each volume of gas is associated with a particular pixel or group of pixels, e.g., pixels of a display device of the image processing system, information corresponding to each of the gas volumes can be used by the image processing system. In particular, the information can be used for digital x-ray imaging, such as real-time x-ray imaging.

Figure 2:
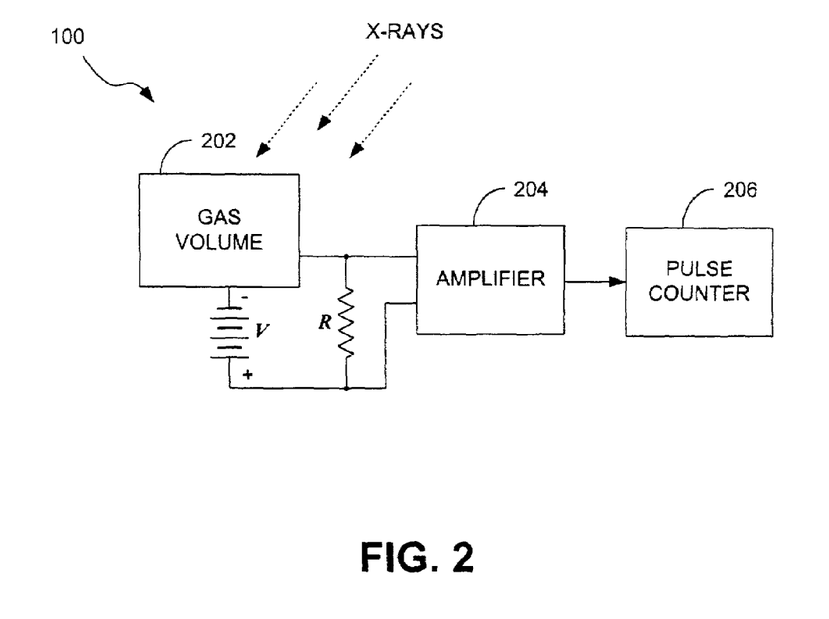
FIG. 2 is a schematic diagram of a representative embodiment of a gas detector that can be used in the x-ray imaging system of FIG. 1.

FIG. 2 schematically depicts a representative embodiment of a pixelated gas detector. In FIG. 2, gas detector 100 includes a gas volume 202 that electrically communicates with an amplifier 204 and a pulse counter 206. The amplifier and pulse counter facilitate a determination of the relative intensity of x-rays incident upon the gas volume. In particular, a potential difference is applied to the gas so that x-rays incident upon the gas volume create ions within the gas. The applied potential difference attracts the ions, thereby generating pulses that are provided to amplifier 204. An amplified signal corresponding to the pulses is then provided from amplifier 204 to pulse counter 206. Pulse counter 206, which is adapted to count the number of pulses occurring during a predetermined interval, then can provide a signal indicative of the intensity of x-rays incident upon the gas volume to an image processing system (see FIG. 1) for processing.

Figure 3:
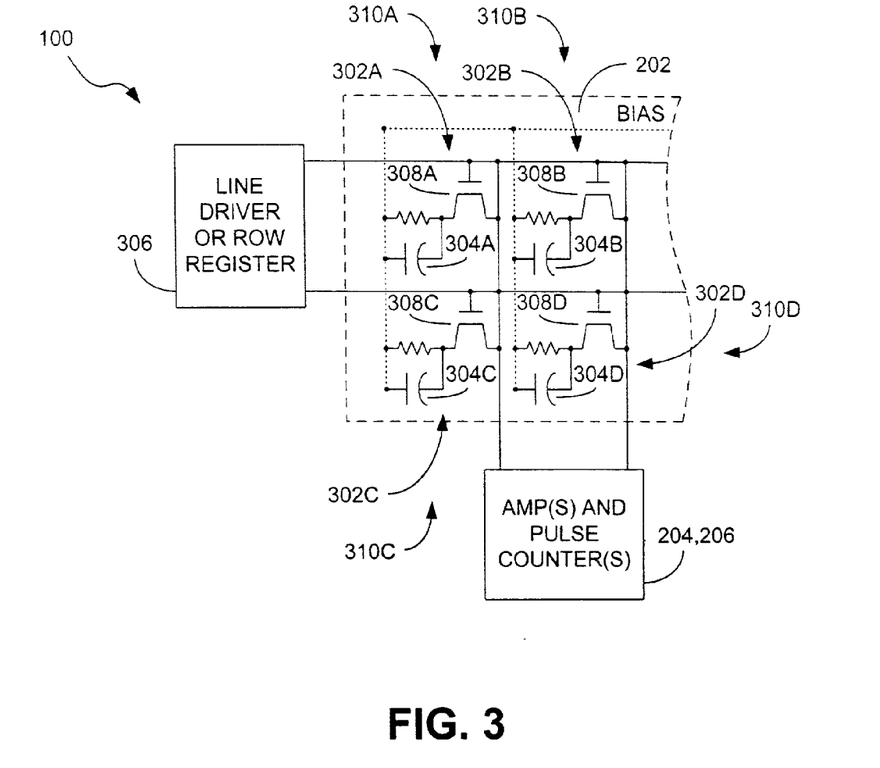
FIG. 3 is a schematic diagram of a representative embodiment of a gas detector that can be used in the x-ray imaging system of FIG. 1.

Another embodiment of gas detector 100 is depicted schematically in FIG. 3. Gas detector 100 of FIG. 3 includes a gas volume 202 that electrically communicates with ion detection circuitry. The ion detection circuitry is used to collect information corresponding to the intensity of x-rays incident upon discrete regions of the gas volume. In particular, multiple ion detection circuits, e.g., circuits 302A, 302B, 302C and 302D, are depicted. Each of the ion detection circuits includes a capacitor, e.g., capacitors 304A, 304B, 304C, and 304D respectively, that is adapted to accumulate a charge representative of the number of ions created within the respective region of the gas volume.

A line driver row register 306 electrically communicates with the ion detection circuits. The row register enables the charges accumulated by the capacitors of the ion detection circuitry to be selectively provided to the amp(s) and pulse counters(s) 204, 206. For instance, in the embodiment of FIG. 3, transistors, e.g., transistors 308A, 308B, 308C, and 308D, coupled between the ion detection circuits and the row register can be selectively biased so that the charge from each ion detection circuit is sequentially provided to the amp(s) and pulse counters(s).

As mentioned before, each of the ion detection circuits is associated with a defined region of gas volume 202. More specifically, circuit 302A is associated with region 310A, circuit 302B is associated with region 310B, circuit 302C is associated with region 310C, and circuit 302D is associated with region 310D. Additionally, each region preferably corresponds to one or more pixels of an image processing system (see FIG. 1). Thus, when ions are created within region 310A, a corresponding charge is accumulated by the capacitor of circuit 302A. Information corresponding to the accumulated charge then can be provided to an image processing system which associates the information with an intensity of x-rays detected in region 310A. The information then can be associated with a designated pixel or group of pixels for processing and/or display, for instance.

Figure 4:
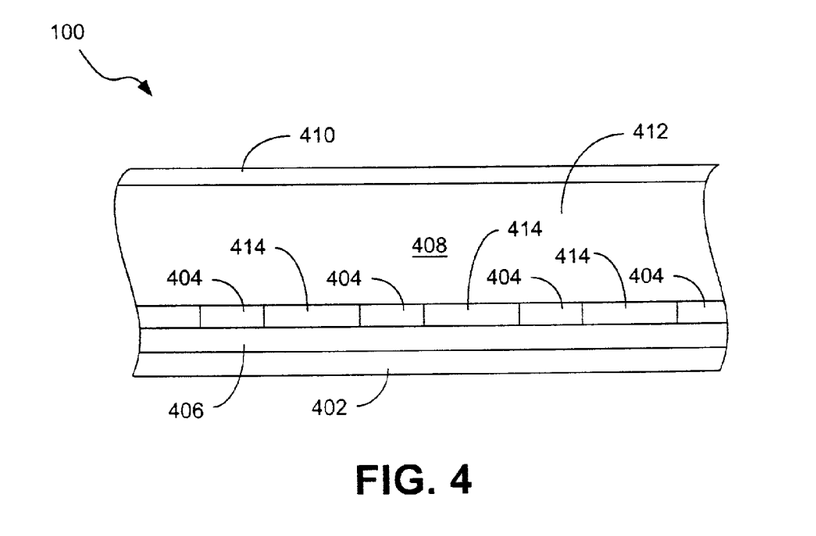
FIG. 4 is a schematic diagram of a representative embodiment of a gas detector that can be used in the x-ray imaging system of FIG. 1.

Referring now to FIG. 4, a representative embodiment of a pixelated gas detector will be described in greater detail. As shown in FIG. 4, gas detector 100 includes a substrate 402. Substrate 402 functions as a support structure for a series of conductive, e.g., metal, vias 404 and detection circuits. Typically, the detection circuits (individual ones of which are not shown in FIG. 4) are arranged in layer 406, with each detection circuit and a corresponding via 404 being associated with a particular region of a volume of gas 408. The metal vias 404 electrically communicate with the gas and enable the detection circuits to detect ions within the gas 408. More specifically, each detection circuit is adapted to detect ions present in a particular region of the gas so that signals corresponding to an intensity of x-rays in that region can be generated. In this configuration, each of the regions of gas preferably corresponds to one or more pixels of an image processing system.

Pixelated gas detector 100 of FIG. 4 also includes an electrode(s) 410 that electrically engages gas volume 408. The electrode(s) are adapted to apply a potential difference to the gas so that ions created by x-rays radiating through the gas are attracted to the detection circuitry through the vias 404. Note, in the embodiment of FIG. 4, the electrode(s) are spaced from the substrate to define a chamber 412 for retaining the volume of gas. In other embodiments, however, various other structures and configurations can be used for retaining the gas, e.g., configurations not using the electrodes to retain the gas.

The pixelated gas detector 100 of FIG. 4, as well as others described herein, can be formed of various materials. By way of example, the gas detector could be formed of a material(s) suitable for manufacture by semiconductor fabrication techniques. For instance, substrate 402 can be $SiO_2$. In such an embodiment, regions 414 arranged between the metal vias as well as portions of layer 406 not attributed to detection circuitry could be formed of substrate material, i.e., $SiO_2$.

Typically, pixelated gas detectors of the invention operate in a counting mode, i.e., the gas detectors count the number of ions created in each of their respectively defined regions, thus, noise is Poisson limited. Applying this limitation to an x-ray imaging application, where noise corresponding to image detection generally is considered approximately 3%, $$0.03 = (1000)^{0.5}/1000;$$

approximately 1000 counts per pixel per image should result in a signal of adequate quality for imaging. For instance, if 24% of 30 keV photons are absorbed in a 1 cm height of Kr at 4 atm, approximately $4 \times 10^3$ photons/pixel should be generated for a signal of adequate quality, i.e., $(4 \times 10^3$ photons/pixel$)(0.24) = 960$ photons/pixel.

Pixelated gas detectors of the invention also could be used for dynamic x-ray imaging, e.g., real time imaging. For instance, cone-beam imaging of an object could be accomplished. A representative example of a pixelated gas detector being used in a dynamic x-ray imaging application is depicted in FIG. 5.

Figure 5:
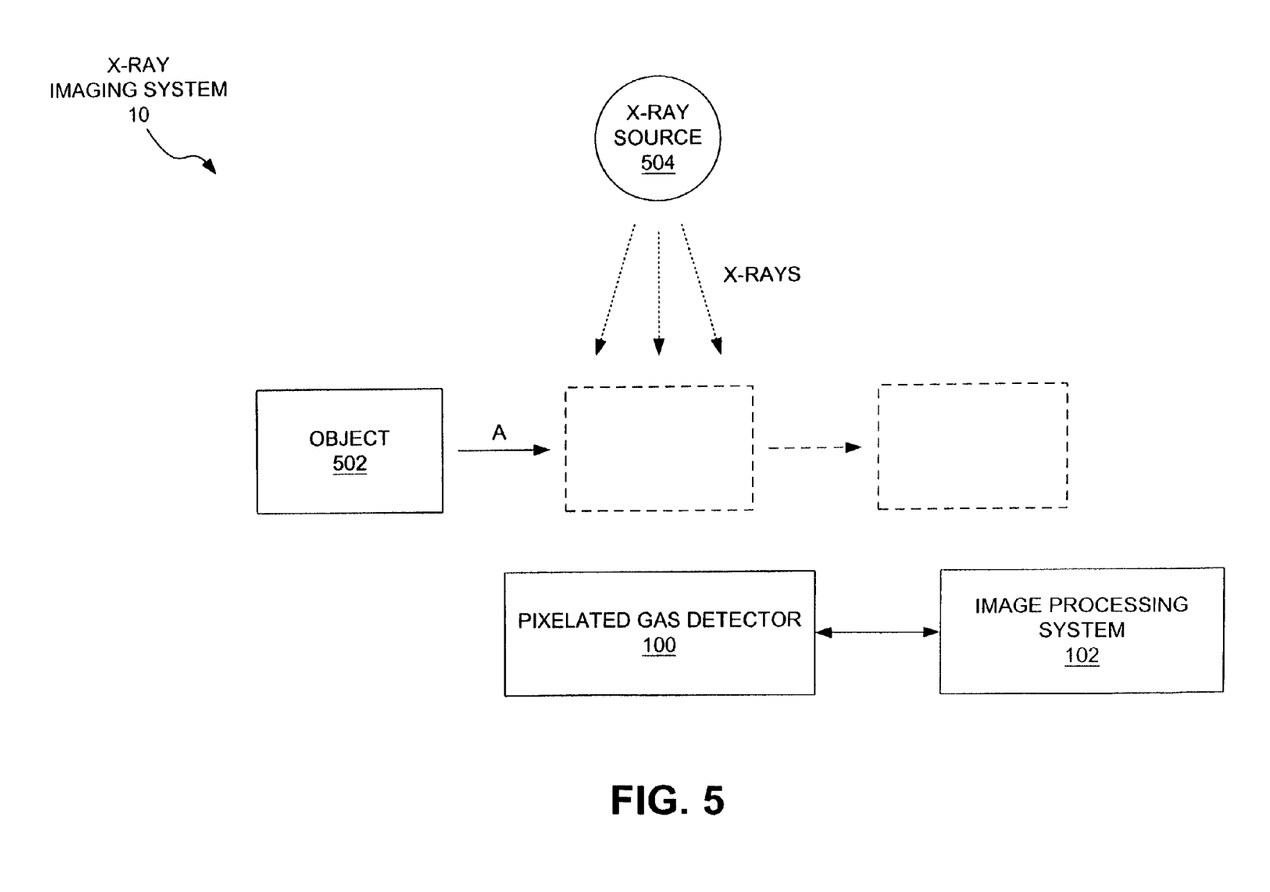
FIG. 5 is a schematic diagram of a representative x-ray imaging system adapted for producing sequential x-ray images of an object.

As shown in FIG. 5, an object 502 is placed approximately 2 cm from an x-ray source 5.4. By using a pixel size of approximately 5 microns, a solid angle of approximately $6.25 \times 10^{-8}$ sr/pixel is substended. Since, at a 100 kV potential, a 0.5 mA x-ray source produces approximately $5 \times 10^{12}$ photons/sr-sec, approximately $3.125 \times 10^5$ photons/pixel-sec are generated. This equates to approximately 80 frames per second. This number is consistent with present needs for x-ray imaging, which runs at approximately 60 frames per second. Thus, by moving object 502 relative to source 504 and gas detector 100, such as by conveying the object in direction A, dynamic x-ray images corresponding to the object can be obtained.

Figure 6:
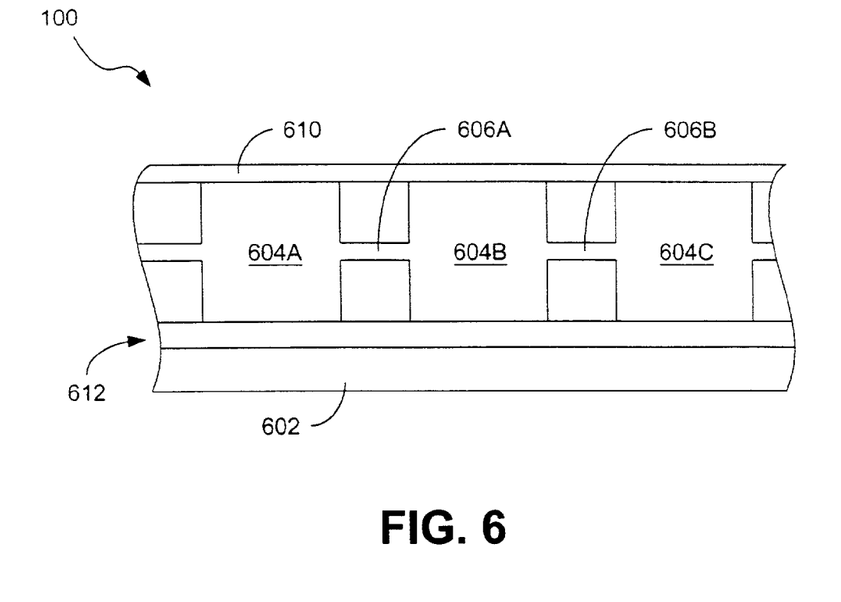
FIG. 6 is a schematic diagram showing detail of several chambers of the gas detector of FIG. 5.
Figure 7:
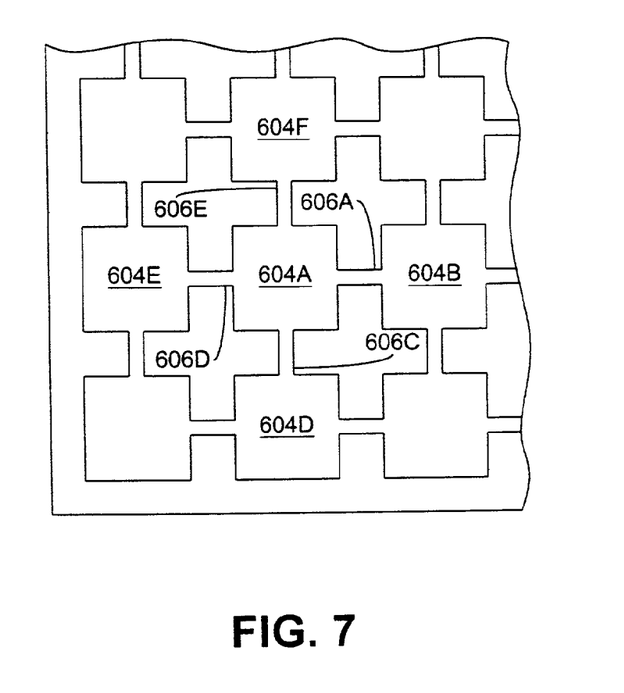
FIG. 7 is a schematic diagram of another representative embodiment of a gas detector.

Another representative embodiment of a pixelated gas detector 100 will be described with reference to FIGS. 6 and 7. As shown in FIG. 6, gas detector 100 includes a substrate 602 that functions as a support structure for a series of chambers. For example, FIG. 6 depicts chambers 604A, 604B and 604C. Each of the chambers defines a region that can be occupied by a volume of gas. In this configuration, each of the chambers preferably corresponds to one or more pixels of an image processing system.

Preferably, at least some of the chambers pneumatically communicate with each other, such as through a series of gas passages, e.g., passages 606A and 606B. As shown in the schematic, plan view of FIG. 7, each chamber can communicate with multiple other chambers. For example, chamber 604A pneumatically communicates with chambers 604B, 604D, 604E and 604F, through vias 606A, 606C, 606D and 606E, respectively.

An electrode(s) 610 electrically engages at least some of the chambers. The electrode(s) are adapted to apply a potential difference to the gas of the chambers so that ions created by x-rays radiating through the gas are attracted to detection circuitry of the gas detector. For instance, the embodiment of FIG. 6 includes detection circuitry 612 arranged between the chambers and the substrate. More specifically, detection circuitry 612 incorporates transmission media (not shown), such as metal vias, that electrically engage the chambers so that electrical signals corresponding to the attracted ions can be provided to various components, e.g., pulse counters (not shown in FIG. 6).

Figure 8:
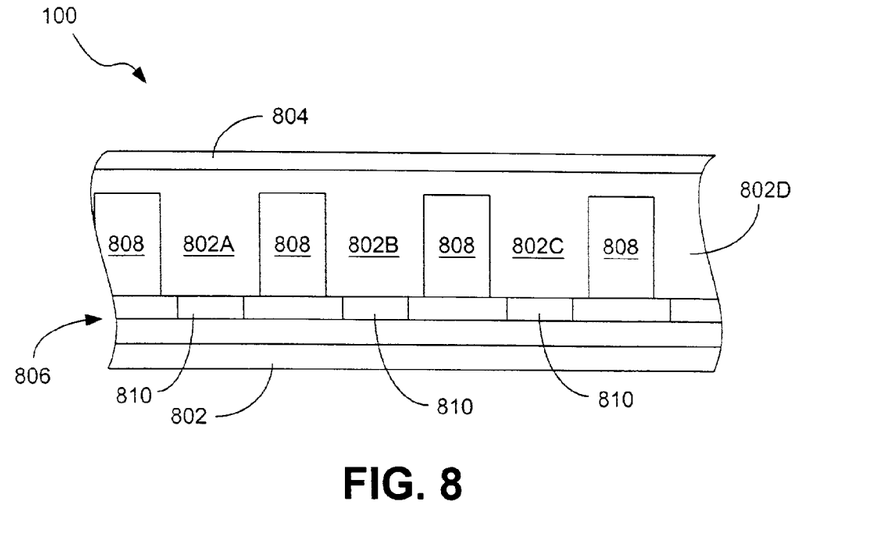
FIG. 8 is a schematic diagram of another representative embodiment of a gas detector.

Another representative embodiment of a pixelated gas detector is depicted in FIG. 8. As shown in FIG. 8, gas detector 100 includes a substrate 802 and a series of chambers, e.g., chambers 802A, 802B, 802C and 802D. Each of the chambers defines a region that can be occupied by a volume of gas and that preferably corresponds to one or more pixels of an image processing system. Like the embodiment of FIG. 6, an electrode(s) 804 electrically engages at least some of the chambers for applying a potential difference to the gas of the chambers. Detection circuitry 806 also is arranged between the chambers and the substrate. Conductive vias 810 also are depicted.

Gas detector 100 of FIG. 8 also includes x-ray stopping components 808 that are arranged between at least some of the chambers. The x-ray stopping components aid in the absorption of off-axis photons, thereby increasing resolution of the detector. The x-ray stopping components can be formed of various materials, such as lead.

As mentioned before, information from the pixelated gas detector can be provided to an image processing system (see system 102 of FIG. 1). Such an image processing system can be implemented in software, firmware, hardware, or a combination thereof. Preferably, image processing system 102 is implemented in software as a program that is executable by a digital computer. An example of a computer that can implement image processing system 102 is shown schematically in FIG. 8.

Figure 9:
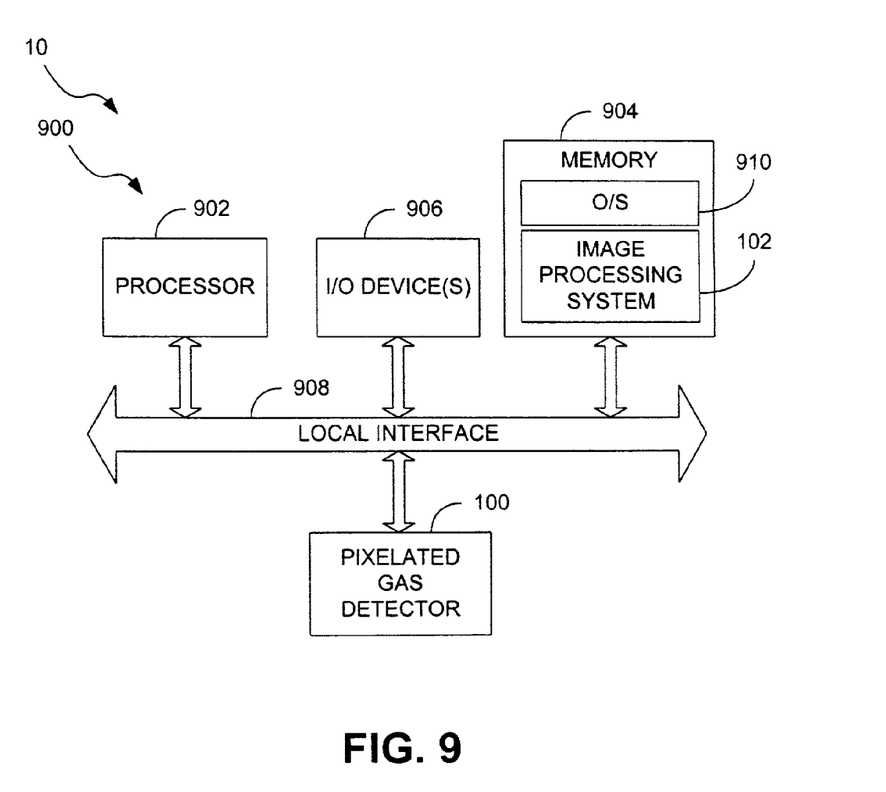
FIG. 9 is a schematic diagram depicting a representative processor-based system that can be used to implement the image processing system of FIG. 1.

Generally, in terms of hardware architecture, computer 900 includes a processor 902, memory 904, and one or more input and/or output (I/O) devices 906 (or peripherals) that are communicatively coupled via a local interface 908. Local interface 908 can be, for example, one or more buses or other wired or wireless connections, as is known in the art. Local interface 908 can include additional elements, which are omitted for ease of description. These additional elements can be controllers, buffers (caches), drivers, repeaters, and/or receivers, for example. Further, the local interface may include address, control, and/or data connections to enable appropriate communications among the components of computer 900.

Processor 902 can be a hardware device configured to execute software that can be stored in memory 904. Processor 902 can be any custom made or commercially available processor, a central processing unit (CPU) or an auxiliary processor among several processors associated with the computer 900. Additionally, the processor can be a semiconductor-based microprocessor (in the form of a microchip), for example.

Memory 904 can include any combination of volatile memory elements (e.g., random access memory (RAM, such as DRAM, SRAM, etc.)) and/or nonvolatile memory elements (e.g., ROM, hard drive, tape, CDROM, etc.). Moreover, memory 904 can incorporate electronic, magnetic, optical, and/or other types of storage media. Note that memory 904 can have a distributed architecture, where various components are situated remote from one another, but can be accessed by processor 902.

The software in memory 904 can include one or more separate programs, each of which comprises an ordered listing of executable instructions for implementing logical functions. In the example of FIG. 7, the software in the memory 904 includes image processing system 102 and a suitable operating system (O/S) 910. The operating system 910 controls the execution of other computer programs, such as image processing system 102. Operating system 910 also provides scheduling, input-output control, file and data management, memory management, and communication control and related services.

The I/O device(s) 906 can include input devices, such as a keypad. I/O device(s) 906 also can include output devices, such as a display device. I/O device(s) 906 may further include devices that are configured to communicate both inputs and outputs.

When computer 900 is in operation, processor 902 is configured to execute software stored within the memory 904, communicate data to and from the memory 904, and generally control operations of the computer 900. Image processing system 102 and O/S 910, in whole or in part, are read by the processor 902, perhaps buffered within processor 902, and then executed.

When image processing system 102 is implemented in software, it should be noted that the image processing system can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

When implemented in hardware, image processing system 102 can be implemented with any or a combination of various technologies. By way of example, the following technologies, which are each well known in the art, can be used: a discrete logic circuit(s) having logic gates for implementing logic functions upon data signals, an application specific integrated circuit (ASIC) having appropriate combinational logic gates, a programmable gate array(s) (PGA), and a field programmable gate array (FPGA).

Figure 10:
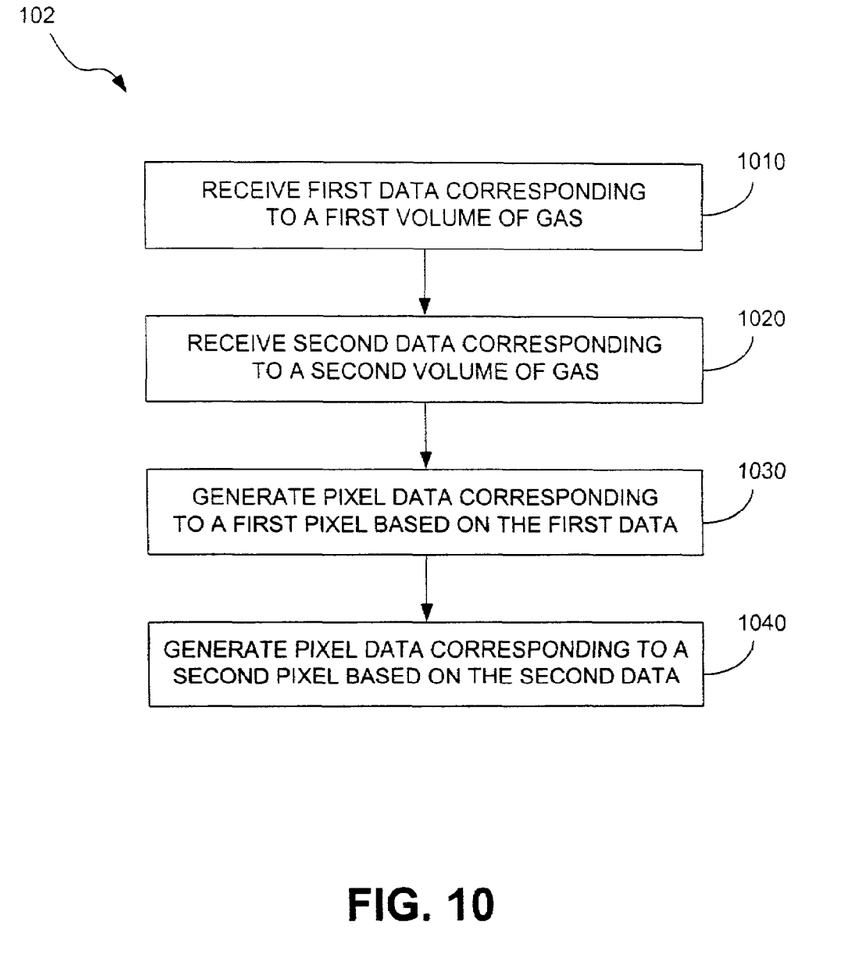
FIG. 10 is a flowchart depicting representative functionality of the image processing system of FIGS. 1 and 7.

The flowchart of FIG. 10 depicts the functionality of a representative implementation of image processing system 102. In this regard, each block of the flowchart represents a module segment or portion of code which comprises one or more executable instructions for implementing the specified logical function(s). It should also be noted that in some alternative implementations the functions noted in various blocks of FIG. 10, or any other of the accompanying flowcharts, may occur out of the order in which they are depicted. For example, two blocks shown in succession in FIG. 10 may, in fact, be executed substantially concurrently. In other embodiments, the blocks may sometimes be executed in the reverse order depending upon the functionality involved.

Referring now to the flowchart of FIG. 10, the functionality of the image processing system or method 102 may be construed as beginning at block 1010 where first information corresponding to a first volume of gas is received. For instance, the information received may correspond to a first region of a volume of gas of a pixelated gas detector, e.g., the first region may be defined by a first chamber. In block 1020, second information corresponding to a second volume of gas is received. First pixel data corresponding to the first information and second pixel data corresponding to the second information is generated in blocks 1030 and 1040 respectively. The first and second pixel data then can be rendered, such as by displaying the pixel data on a display device.

Figure 11:
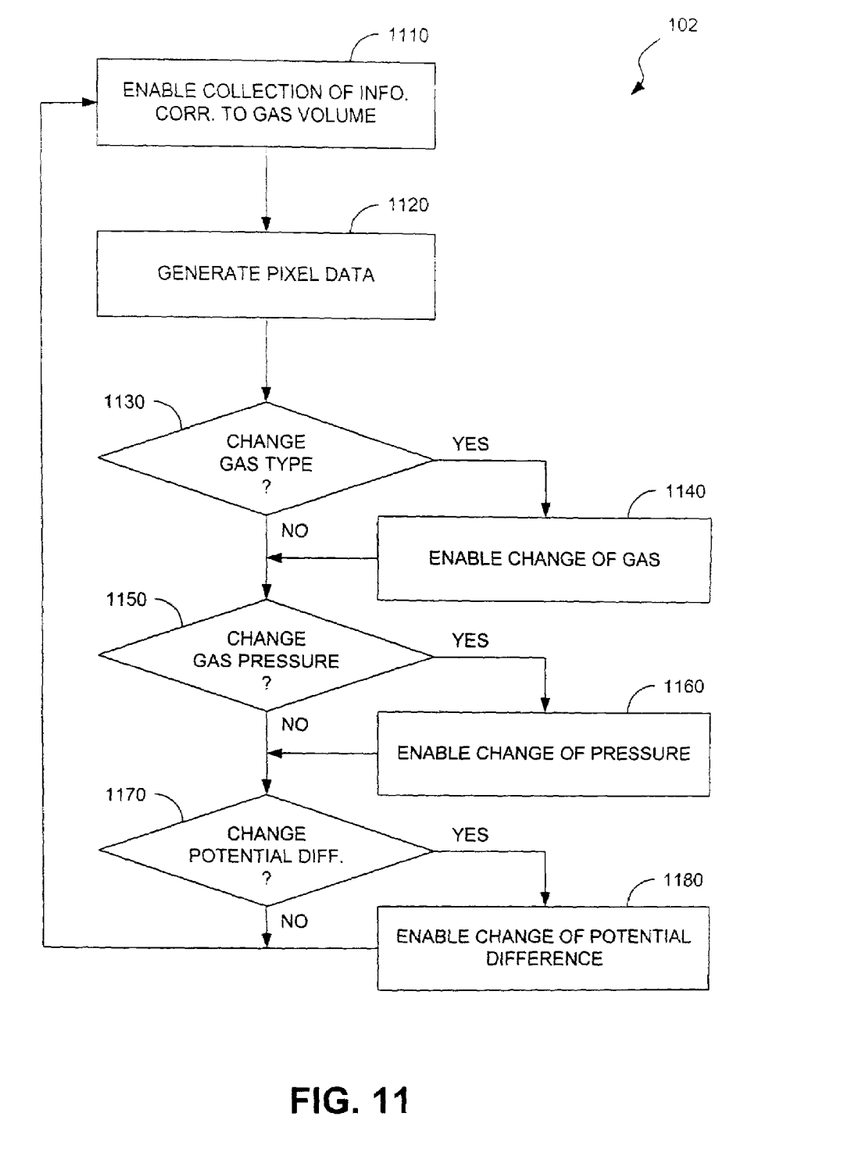
FIG. 11 is a flowchart depicting representative functionality of an alternative embodiment of the image processing system of FIGS. 1 and 7.

The functionality of another implementation of the image processing system or method 102 is depicted in the flowchart of FIG. 11. In FIG. 11, the image processing system or method 102 may be construed as beginning at block 1110, where collection of information corresponding to a gas volume is enabled. Proceeding to block 1120, generation of pixel data corresponding to the gas volume is enabled. The remaining blocks of the flowchart of FIG. 11 may be generally regarded control functionality that can be used by embodiments of an x-ray imaging system of the invention to facilitate collection of information. More specifically, blocks 1130 through 1180 relate to various aspects of controlling a pixelated gas detector. In other embodiments, pixelated gas detector control functionality, such as the functions depicted in blocks 1130 through 1180, may not be implemented by the image processing system.

Referring now to block 1130, the image processing system may determine whether the gas used in the pixelated gas detector should be changed. For instance, since different gasses exhibit different levels of photoabsorptivity, it may be desirable in some applications to modify and/or replace the gas used in a pixelated gas detector in order to alter the sensitivity of the gas detector to x-rays. If it is determined that the gas is to be changed, the process preferably proceeds to block 1040, where changing of the gas is enabled.

After block 1140 or, alternatively, block 1130, a determination may be made as to whether the pressure of the gas used in the pixelated gas detector should be changed (block 1150). Change of gas pressure also affects the photoabsorptivity of the gas. If it is determined that the pressure of the gas is to be changed, the process preferably proceeds to block 1160, where changing of the gas pressure is enabled.

After block 1160 or, alternatively, block 1150, a determination may be made as to whether the potential difference applied to the gas used in the pixelated gas detector should be changed (block 1170). More specifically, it may be desirable to change or tune the potential difference to improve or otherwise change the produced signal.

Figure 12:
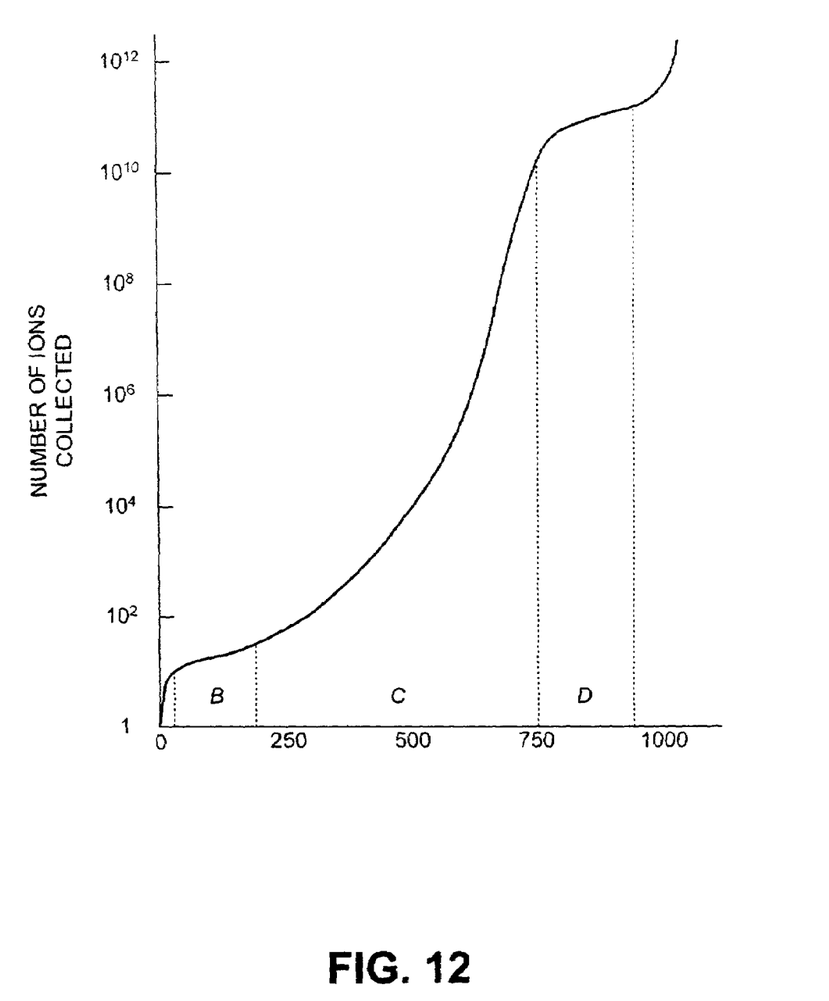
FIG. 12 is a graph depicting number of ions collected versus voltage for a representative gas detector.

Change of applied potential difference affects the operation of a gas detector as shown in FIG. 12. For instance, it can be seen that operation of a gas detector in voltage regime B causes the gas detector to behave as an ionization chamber, whereas operation of the gas detector in voltage regime C causes the gas detector to behave as a proportional counter. Therefore, if the extraction of energy spectral information is desired, the operating regime of the gas detector can be changed to C. If the potential difference applied to the gas is to be changed, the process preferably proceeds to block 1180, where changing of the potential difference is enabled.

Figure 13:
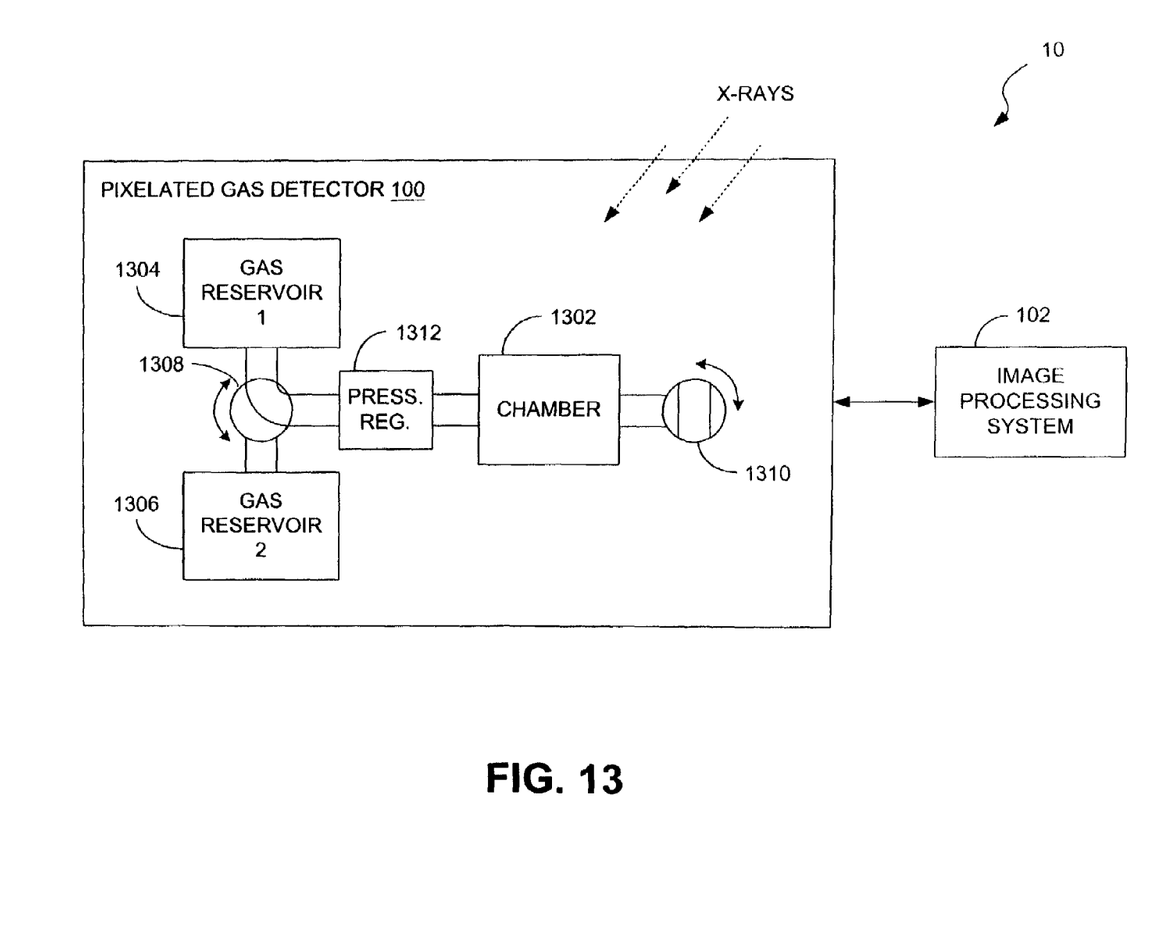
FIG. 13 is a schematic diagram of another representative embodiment of an x-ray imaging system of the invention.

A representative embodiment of an x-ray imaging system that can be used to implement the functionality of the image processing system of FIG. 11 is depicted in FIG. 13. As shown in FIG. 13, x-ray imaging system 10 includes a pixelated gas detector 100 and an image processing system 102. Gas detector 100 incorporates one or more chambers 1302, each of which preferably is adapted to retain a volume of gas. Gas for filling the chamber(s) is provided by a source, such as a gas reservoir. In the embodiment of FIG. 13, two such reservoirs are provided. More specifically, a first gas reservoir 1304 and a second gas reservoir 1306 are adapted to provide gas, which may be of different types, to the chamber(s). Selection of an appropriate gas(es) can be based on known properties, such as those described in Atomic Data and Nuclear Data Tables by B. L. Henke, E. M. Gullikson, and J. C. Davis, which is incorporated herein by reference. Note, in other embodiments additional sources of gas can be used.

An input valve 1308 coupled between the reservoirs and the chamber(s) enables gas to be delivered selectively to the chamber(s) from each of the reservoirs. An output valve 1310 also is provided which, in an open position, enables gas from the chamber(s) to be evacuated and, in a closed position, enables gas to fill the chamber(s) and/or to be pressurized within the chamber(s). For instance, when gas from gas reservoir 1304 is desired in the chambers, the image processing system can provide a control signal to output valve 1310 so that the valve moves to its open position. An additional control signal can be provide to input valve 1308 so that gas from gas reservoir 1304 is able to enter the chamber(s). Initially, the gas from the first gas reservoir can be used to flush the chamber(s). Thereafter, another control signal can be sent to the output valve so that the valve moves to its closed position. In this manner, the chamber(s) can be filled with gas from the first gas reservoir.

A pressure regulator 1312 also is coupled between the gas reservoir(s) and the chamber(s). In embodiments incorporating a pressure regulator, an increase in the pressure of the gas maintained within the chamber(s) can be achieved by adjusting the regulator in response to a control signal of the image processing system. Additionally, a reduction in pressure could be achieved by selective venting of gas from the chamber(s) via the output valve and/or via adjustment of the pressure regulator.

The foregoing description has been presented for purposes of illustration and description. It is not intended to be exhaustive or to limit the invention to the precise forms disclosed. Modifications or variations are possible in light of the above teachings. The embodiment or embodiments discussed, however, were chosen and described to provide the best illustration of the principles of the invention and its practical application to thereby enable one of ordinary skill in the art to utilize the invention in various embodiments and with various modifications as are suited to the particular use contemplated. All such modifications and variations, are within the scope of the invention as determined by the appended claims.

The invention claimed is:

1. An x-ray imaging system comprising:
   a substrate comprising material compatible with a semiconductor manufacturing process; and
   a gas detector formed on the substrate, the gas detector comprising a first detection circuit corresponding to a first chamber and a second detection circuit corresponding to a second chamber, said first detection circuit providing a first signal indicative of an intensity of a first portion of x-rays radiating into the first chamber, said second detection circuit providing a second signal indicative of an intensity of a second portion of x-rays concurrently radiating into the second chamber, the first portion of x-rays being different than the second portion of x-rays, and wherein an x-ray stopping component is arranged between said first and second chambers, the x-ray stopping component operative to absorb off-axis photons.

2. The x-ray imaging system of claim 1, further comprising:
   means for changing a pressure of the volume of gas.

3. The x-ray imaging system of claim 1, further comprising:
   means for changing the gas from one type of gas to another type of gas.

4. An x-ray imaging system comprising:
   a gas detector comprising a first detection circuit corresponding to a first chamber and a second detection circuit corresponding to a second chamber, said first detection circuit providing a first signal indicative of an intensity of a first portion of x-rays radiating into the first chamber, said second detection circuit providing a second signal indicative of an intensity of a second portion of x-rays concurrently radiating into the second chamber, the first portion of x-rays being different than the second portion of x-rays, and wherein an x-ray stopping component is arranged between said first and second chambers, the x-ray stopping component operative to absorb off-axis photons;
   a first gas reservoir selectively, pneumatically communicating with said first chamber; and
   a second gas reservoir selectively, pneumatically communicating with said first chamber such that gas from either said first gas reservoir or said second gas reservoir can be selectively provided to said first chamber.

5. A method for imaging with the use of x-rays, said method comprising:
   providing a substrate;
   using a semiconductor fabrication technique to form on the substrate, a first chamber, a second chamber, and an x-ray stopping component between the first chamber and the second chamber;
   generating a first signal indicative of an intensity of a first portion of x-rays radiating into the first chamber, the first signal corresponding to at least a first pixel; and
   generating a second signal indicative of an intensity of a second portion of x-rays concurrently radiating into the second chamber, the second signal corresponding to at least a second pixel, wherein the first portion of x-rays is different than the second portion of x-rays.

6. The method of claim 5, further comprising:
rendering the first pixel based on the first signal; and
rendering the second pixel based on the second signal.

7. The method of claim 5, further comprising:
changing a pressure of a volume of gas within the first chamber.

8. The method of claim 5, further comprising:
providing an object to be imaged, the object being arranged at least partially between a source of x-rays and at least one of the first and second chambers;
generating additional signals indicative of the intensity of x-rays radiating into the first and second chambers; and
generating sequential images corresponding to the object based on the additional signals.

9. The method of claim 8, further comprising:
moving the object relative to at least one of the first and second chambers while the object is being radiated.

10. A pixelated gas detector comprising:
a first chamber;
a first detection circuit providing a first signal indicative of an intensity of a first portion of x-rays radiating into the first chamber;
a second chamber;
a second detection circuit providing a second signal indicative of an intensity of a second portion of x-rays concurrently radiating into the second chamber;
an x-ray stopping component arranged between the first and second chambers, the x-ray stopping component operative to absorb off-axis photons; and
a first and a second gas reservoir pneumatically communicating with the first chamber such that gas from either the first or the second gas reservoir can be selectively provided to the first chamber.

11. The pixelated gas detector of claim 10, further comprising:
a pressure regulator for setting a first pressure of gas in the first chamber.

12. The pixelated gas detector of claim 10, wherein the x-ray stopping component comprises lead.

* * * * *